(12) United States Patent
Foster (10) Patent No.: US 8,740,386 B2
(45) Date of Patent: Jun. 3, 2014

(54) AUTOMATED VISION SCREENING APPARATUS AND METHOD

(75) Inventor: Bart Foster, Winchester (GB)

(73) Assignee: Solohealth, Inc., Duluth, GA (US)

( * ) Notice: Subject to any disclaimer, the term of this patent is extended or adjusted under 35 U.S.C. 154(b) by 0 days.

(21) Appl. No.: 13/440,804

(22) Filed: Apr. 5, 2012

(65) Prior Publication Data

US 2012/0188507 A1 Jul. 26, 2012

Related U.S. Application Data (63) Continuation of application No. 12/364,925, filed on Feb. 3, 2009, now Pat. No. 8,182,091, which is a continuation-in-part of application No. 10/985,524, filed on Nov. 10, 2004, now Pat. No. 7,614,747.

(60) Provisional application No. 60/591,670, filed on Jul. 28, 2004.

(51) Int. Cl.
*A61B 3/10* (2006.01)
*A61B 3/02* (2006.01)
*A61B 3/00* (2006.01)

(52) U.S. Cl.
USPC .......................... 351/246; 351/205; 351/223

(58) Field of Classification Search
USPC .................................................. 351/200–246
See application file for complete search history.

(56) References Cited

U.S. PATENT DOCUMENTS

| | | |
|---|---|---|
| 4,105,302 A | 8/1978 | Tate, Jr. |
| 4,869,589 A | 9/1989 | Blair et al. |
| 5,914,772 A | 6/1999 | Dyer |
| 5,929,972 A * | 7/1999 | Hutchinson ............ 351/237 |
| 6,422,700 B2 | 7/2002 | Ohyagi |
| 6,450,643 B1 | 9/2002 | Wilson |
| 6,540,643 B2 * | 4/2003 | Ohtsuka ................. 477/83 |
| 6,592,223 B1 | 7/2003 | Stern et al. |
| 6,594,607 B2 | 7/2003 | Lavery |
| 6,687,389 B2 | 2/2004 | McCartney et al. |
| 6,726,633 B2 | 4/2004 | Kitagawa |
| 6,761,453 B2 | 7/2004 | Wilson |
| 6,899,428 B2 * | 5/2005 | Mihashi ................. 351/239 |
| 7,233,312 B2 * | 6/2007 | Stern et al. ............. 345/156 |
| 7,350,921 B2 | 4/2008 | Ridings |
| 7,437,344 B2 | 10/2008 | Peyrelevade |

(Continued)

FOREIGN PATENT DOCUMENTS

| | | |
|---|---|---|
| JP | 2001-286442 | 10/2001 |
| JP | 2002-10977 | 1/2002 |

(Continued)

OTHER PUBLICATIONS

U.S. Appl. No. 12/545,405, electronically captured on Aug. 9, 2013 for Feb. 4, 2013 to Aug. 9, 2013.

(Continued)

*Primary Examiner* — Mohammed Hasan
(74) *Attorney, Agent, or Firm* — DLA Piper LLP US (57) ABSTRACT

A method for screening vision using a kiosk comprising: requesting, using the kiosk, user information; performing objective visual acuity tests using the kiosk, wherein said visual acuity tests determine: sphere, cylinder, cylinder axis, or corneal curvature, or any combination thereof; and reporting visual acuity results, wherein said method does not require assistance from another person.

14 Claims, 9 Drawing Sheets

(56) References Cited

U.S. PATENT DOCUMENTS

| | | |
|---|---|---|
| 2001/0025226 A1 | 9/2001 | Lavery |
| 2002/0021411 A1 | 2/2002 | Wilson |
| 2002/0080329 A1 | 6/2002 | Kasahara |
| 2003/0020877 A1* | 1/2003 | Marrou ............ 351/246 |
| 2003/0058404 A1 | 3/2003 | Thorn et al. |
| 2003/0065636 A1 | 4/2003 | Peyrelevade |
| 2003/0117580 A1 | 6/2003 | Franz et al. |
| 2003/0208190 A1* | 11/2003 | Roberts et al. ............ 606/5 |
| 2004/0076942 A1 | 4/2004 | O'Neil et al. |
| 2004/0141152 A1 | 7/2004 | Marino et al. |
| 2005/0273359 A1 | 12/2005 | Young |
| 2006/0023163 A1 | 2/2006 | Foster |
| 2009/0228304 A1 | 9/2009 | Ciarniello et al. |
| 2009/0310084 A1 | 12/2009 | Foster |
| 2010/0033678 A1 | 2/2010 | Foster |
| 2011/0299034 A1* | 12/2011 | Walsh et al. ............ 351/206 |
| 2012/0188507 A1 | 7/2012 | Foster |

FOREIGN PATENT DOCUMENTS

| | | |
|---|---|---|
| JP | 2002-78679 | 3/2002 |
| JP | 2002-78681 | 3/2002 |
| JP | 2002-83156 | 3/2002 |
| JP | 2002-238858 | 8/2002 |
| JP | 2003-57021 | 2/2003 |
| JP | 2003-57038 | 2/2003 |
| JP | 2003-75785 | 3/2003 |
| JP | 2003-228623 | 8/2003 |
| JP | 2004-33637 | 2/2004 |
| JP | 2004-34893 | 2/2004 |
| WO | WO 03/007392 | 1/2003 |
| WO | WO 2006/010611 | 2/2006 |
| WO | WO 2006/029048 | 3/2006 |

OTHER PUBLICATIONS

Panaseca, Inc., "Welcome to the Eye Advisor: Your Self-Care Eye Health Information Center", Copyright 2003, pp. A1-A18.
Panaseca, Inc., "Panaseca Office Pro", Date Unknown, pp. B1-B4.
Bruce Solomon, "Vision Centers by Panaseca", Jan. 27, 2005, pp. 1-7.
Office Action issued in Japanese Application No. 2007-523014, mailed Jan. 5, 2011.
English language translation of Office Action issued in Japanese Application No. 2007-523014, mailed Jan. 5, 2011.
English language abstract of JP 2002-83156, published Mar. 22, 2002.
Machine English language translation of JP 2002-83156, published Mar. 22, 2002.
English language abstract of JP 2002-78681, published Mar. 19, 2002.
Machine English language translation of JP 2002-78681, published Mar. 19, 2002.
English language abstract of JP 2002-78679, published Mar. 19, 2002.
Machine English language translation of JP 2002-78679, published Mar. 19, 2002.
English language abstract of JP 2003-228623, published Aug. 15, 2003.
Machine English language translation of JP 2003-228623, published Aug. 15, 2003.
English language abstract of JP 2002-238858, published Aug. 27, 2002.
Machine English language translation of JP 2002-238858, published Aug. 27, 2002.
English language abstract of JP 2004-34893, published Feb. 5, 2004.
Machine English language translation of JP 2004-34893, published Feb. 5, 2004.
English language abstract of JP 2004-33637, published Feb. 5, 2004.
Machine English language translation of JP 2004-33637, published Feb. 5, 2004.
English language abstract of JP 2003-57038, published Feb. 26, 2003.
Machine English language translation of JP 2003-57038, published Feb. 26, 2003.
English language abstract of JP 2003-57021, published Feb. 26. 2003.
Machine English language translation of JP 2003-57021, published Feb. 26, 2003.
English language abstract of JP 2003-75785, published Mar. 12, 2003.
Machine English language translation of JP 2003-75785, published Mar. 12, 2003.
English language abstract of JP 2001-286442, published Oct. 16, 2001.
Machine English language translation of JP 2001-286442, published Oct. 16, 2001.
English language abstract of JP 2002-10977, published Jan. 15, 2002.
Machine English language translation of JP 2002-10977, published Jan. 15, 2002.
U.S. Appl. No. 12/364,925, electronically captured on Feb. 4, 2013.
U.S. Appl. No. 12/545,405, electronically captured on Feb. 4, 2013.
U.S. Appl. No. 10/985,524, electronically captured on Feb. 4, 2013.
U.S. Appl. No. 09/783,449, electronically captured on Feb. 4, 2013
International Search Report issued in International Application No. PCT/EP2005/008158, mailed Nov. 28, 2005.
Written Opinion issued in International Application No. PCT/EP2005/008158, mailed Nov. 28, 2005.
Office Action issued in EP 05778082.7, mailed Sep. 16, 2009.
Office Action issued in EP 05778082.7, mailed Feb. 2, 2010.
Office Action issued in EP 05778082.7, mailed Jun. 2, 2010.
Office Action issued in EP 06778082.7, mailed Jan. 10, 2011.
U.S. Appl. No. 12/545,405.

* cited by examiner

Thank you for using EyeSite automated vision screening

EyeSite

This vision screening is only an estimate of your current sight.
It can indicate that you need to get an eye exam, but
it does not serve as a substitute for a comprehensive eye exam.

Your Distance Vision is:

LEFT EYE 20/10                     RIGHT EYE 20/20

LEFT EYE / RIGHT EYE
What this means:

20/20 Normal Vision. It means a
person can clearly see an object from
20 feet that the average person with
normal vision can see at the same
distance.

20/30 You can see at 20 feet what
the average person with normal
vision can see at 30 feet.

20/40 You can see at 20 feet what
the average person with normal
vision can see at 40 feet.

20/60 You can see at 20 feet what
the average person can see
at 60 feet.

To have your eyes properly evaluated, please make an appointment
with a qualified optician for a comprehensive eye examination.

A comprehensive eye examination will involve careful testing of
all aspects of your vision. Based upon the results of your exam,
the eye care professional will then recommend a treatment plan
for your individual needs. Remember, only an eye care
professional can provide a comprehensive eye exam – most family
physicians and pediatricians are not fully trained to do this,
and studies have shown that they can miss important vision problems
that require treatment.

Treatment plans can include glasses or contact lenses for blur,
eye exercises or surgery for muscle problems, medical treatment
for eye disease or simply a recommendation that you have your
eyes examined again in another couple of years.

No matter who you are, regular eye exams are important for
seeing more clearly, learning more easily and preserving your
vision for life.

Present this voucher to one of the
following opticians near you and receive
$5 OFF
a complete eye examination

XYZ Opticians, 104 St. Cross Road, Winchester
ABC Optical, 200 Mead Road, Winchester
Spectacles, 123 St. Cross Road, Winchester
*Offer Expires: 10/31/2004

FREE

NIGHT & DAY Trial
plus $20 OFF your first purchase
Please present this voucher to your
local optician.
*Offer Expires 10/31/2004

AUTOMATED VISION SCREENING APPARATUS AND METHOD

CROSS REFERENCE TO RELATED APPLICATION

This application is a continuation of U.S. patent application Ser. No. 12/364,925, filed Feb. 3, 2009 now U.S. Pat. No. 8,182,091 B2, which is a continuation-in-part of U.S. patent application Ser. No. 10/985,524, filed Nov. 10, 2004 now U.S. Pat. No. 7,614,747 B2, which, in turn, claims the benefit under 35 USC §119(e) of U.S. Provisional Application No. 60/591,670, filed Jul. 28, 2004, which are incorporated by reference in their entireties.

TECHNICAL FIELD

An automatic self-service vision screening kiosk and method that allows individuals to screen their eyesight without assistance. The device includes subjective and/or objective tests via an interactive video and software program that measures visual acuity and contrast sensitivity. The device is designed to provide a report with test results. The device and method may also provide a means for making referrals, scheduling appointments, ordering lenses, dispensing lenses, and/or forwarding prescriptions to eye care professionals or lens manufacturers.

BACKGROUND OF THE INVENTION

An estimated 164 million Americans require some form of vision correction. In 1999, only about 52 percent of persons needing vision correction purchased eyewear, leaving 48 percent, who purchased nothing.

The American Optometric Association recommends that a patient visit an optometrist every 1-2 years because eyesight can deteriorate slowly, making self-diagnosis difficult. Less than thirty percent of Americans that are age 40 and over realize the importance of regular eye exams. Two major reasons why consumers fail to visit their optometrist regularly are based upon convenience and belief that their vision remains static.

In order to accurately test a person's distance vision, the subject typically stands a significant distance, sometimes 20 ft, from the stimulus or visual target. The examiner asks the subject to read aloud the letters corresponding to a given line on a chart, and each line going down the chart has smaller letters. This is typically referred to as the Snellen test, using a Snellen chart to display the different letter sizes and specific letters.

There are vision screener products on the market that try to overcome the need to have a significant distance between the chart and the subject, in order to accurately test one's vision in a small compact device. Some applications use lenses to magnify or minimize the stimulus letter and then present said letters only a few inches away from the subject's eyes. This form of screener leads to common testing errors called induced myopia. The brain-to-eye system in the human body recognizes that the stimulus is located so close and causes the eyes to become cross-eyed to focus, thereby causing myopic results.

Additionally, some segments of the general population are unable to take a typical exam performed in doctors' offices. For example, some consumers have special needs and may not comprehend the Snellen test. Other consumers, such as very young children may not be able to differentiate letters, numbers or other shapes used to diagnose vision defects. Other consumers may fear the expense of a lengthy eye exam in countries that require an exam for a vision correction prescription. Still other consumers may have a language barrier that makes a Snellen or refractive exam difficult or impossible.

Some countries do not require prescriptions for corrective lenses; however, individuals who do not know their sphere and cylinder corrections cannot accurately determine which lenses to order. Additionally, in some countries, eye care professionals may not be accessible to all individuals. In these countries, some individuals requiring vision correction may not have access to: 1) methods to indicate the type and power of vision correction needed; and 2) methods to obtain vision correction.

SUMMARY OF THE INVENTION

The present invention provides a device and method for measuring and reporting visual acuity at the user's convenience. The present invention also seeks to provide a means for a user to manage his or her optical health by providing referrals to eye care professionals and corrective lens producers. The invention may also provide a means for electronic communication between a user, a practitioner and/or a corrective lens supplier/producer, and/or an eye care professional. The present invention may also provide an interactive eye care makeover that allows a user to experience varying types of vision correction.

In one embodiment, the invention comprises a method for screening vision without assistance at a kiosk, the method including the steps of requesting user information, performing visual acuity tests, and reporting visual acuity results. In, one embodiment, objective visual acuity tests are performed by an automated adaptive optic phoropter, a badal optometer, a corneal topographer, a tonomer, a wavefront sensor, and/or a Fundus camera. In another embodiment, subjective tests, such as a Snellen test or a Landolt C test are automated. In another embodiment, other tests, such as tests for glaucoma or color vision deficiency may be performed. The invention preferably determines subjectively or objectively based visual acuity at distance and near. In another embodiment, the patient's refractive error, including sphere, cylinder, and cylinder axis are provided. In still another embodiment the results are reported at the user kiosk or via the Internet to a third party, which may include an eye care professional, a lens supplier, a lens distributor, a lens manufacturer and/or a web database. In one embodiment, the results may be reported via a SmartCard®.

In another embodiment; the invention may be used to provide referrals to, or schedule appointments with, an eye care professional. In an alternative embodiment, the present invention may perform a virtual eye care makeover. In still another embodiment, the invention may dispense piano lenses. In one embodiment, the invention requests and collects payment from a consumer.

The invention also provides a user kiosk for automatic visual acuity screening that includes vision test instrumentation, at least one microprocessor, a shell, a WAN/LAN connection, a communication means, and/or a reporting means. The kiosk also provides a stimulus and a plurality of mirrors. The stimulus projects an image onto a first mirror and the mirror reflects the image onto further mirrors positioned at particular angles. The invention may also include a credit and coin payment device, remote management software, a digital camera, and/or Customer Relationship Management System (CRM). In one embodiment the communication means may be a visual communication means, which may be a touch screen or a keyboard. In another embodiment, the invention may include an audio communication means.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE EXAMPLE EMBODIMENTS

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the procedures are well known and commonly employed in the art. Conventional methods are used for these procedures, such as those provided in the art and various general references. Where a term is provided in the singular, the inventor also contemplates the plural of that term. The nomenclature used herein and the devices and procedures described below are those well known and commonly employed in the art. All patents listed herein are expressly incorporated by reference in their entirety.

Currently, vision screening may be performed by an optometrist or ophthalmologist in a medical/office environment. During an exam, many different tests may be performed to obtain a full measurement of visual acuity and/or contrast sensitivity. Vision tests may vary according to the practitioner and patient. Additionally, some countries do not require a prescription to purchase certain types of vision correction, such as, for example, contact lenses. In these countries, consumers may simply purchase vision correction from a retailer or supplier.

Testing refractive errors of the eye involves several tests, some of which are subjective, and others that are objective in nature. Objective refraction tests include the use of well known retinoscopy and autorefractors, while subjective refractions include a variety of interactive tests. Comprehensive refractive error testing typically determines the patient's sphere, cylinder and cylinder axis.

When subjective tests are used, targets may be presented to a subject with a projector, with illuminated wall charts, or with an LCD panel and software, or via a video screen. One of the most well-known subjective tests is the Snellen test. The Snellen test consists of several lines of letters. The letters on the top line are the largest; those on the bottom line are the smallest. To test sight at far distances, the test is routinely taken about 20 ft (6 m) from the chart. Typically, the patient covers one eye and reads the smallest visible line of letters. The patient then repeats the process for the other eye. A tumbling E chart may be used to test vision for children and for people who cannot read. The E chart is similar to the Snellen chart in that there are several lines, but all of the lines contain only the letter E in different positions. The top line is the largest and the bottom line of Es is the smallest. The person is asked to indicate the direction of the E. Similar charts use the letter C, such as the Landolt test, or pictures. A subjective means of determining the refractive error includes the use of a vision target and involves manually changing lenses with a manual phoropter, for example see U.S. Pat. No. 5,223,864, or using trial frames.

Automated devices can be used for more objective testing, particularly testing for refractive errors of the eye. Such devices include autorefractors, autolensometers, and autophoropters. For example U.S. Pat. No. 3,880,501 discloses a system for measuring refraction of eye that can be used manually or with automated refractors. U.S. Pat. No. 5,329,322 discloses use of an autorefractor to obtain refractions objectively and in a rapid manner using two images, and their reflected images, for differential comparison. A phoropter can be manipulated by a control unit so that an operator's movement can be minimized during the testing procedure (see U.S. Pat. No. 4,861,156). U.S. Pat. No. 5,331,394 also discloses an autolensometer.

In one embodiment of the present invention, an autorefractor may be used. An autorefractor is an automated objective refracting instrument operated by a simple button push. This instrument is used to obtain an initial measurement of the patient eye being tested. No patient response is obtained. The autorefractor result has regression equations for the three components of sphere, cylinder and cylinder axis applied to it to produce a corrected autorefractor result. The corrected autorefractor result is used as a starting point for the remainder of the test, which may be subjective in nature. Similarly, an autolensometer is used to objectively obtain the refractive power of eye glasses or contact lenses. Measurements may be transmitted to a system computer and stored in a memory file.

Modern autolensometers can perform the usual functions of neutralization and verification without the aid of human interpretation and may also perform related tasks, such as laying out progressives, determining cut-out, and blocking up lenses. Most also have the ability to communicate with other digital equipment, such as phoropters and blockers. The autorefractor, corrected autorefractor, and autolensometer may operate without user input and may be wholly objective.

Wavefront sensors may also be used to detect refractive errors in the eye, such as for example, a Shack-Hartmann wavefront sensor. Measurements of the wavefront aberrations of the eye to a high degree of precision using an improved Hartmann-Shack wavefront sensor are described in U.S. Pat. No. 5,777,719. The wavefront sensor shines a narrow light or LED on the retina and fits any astigmatic errors to the Zernike index. Starting at the retina, an ideal wavefront is generated which passes through the optical path of the eye. As the wavefront exits the eye, it contains a complete map of the eye's aberrations for analysis by the sensor. Once the wavefront is received by the sensor, a complex series of analyses are performed to provide a "complete" picture of the eye's optical path.

Typically, when tests are administered in an eye care professional's office, the patient may not fully understand the results of the test. Oftentimes the patient may order corrective lenses at the same location and the process is seamless; the patient never views his or her prescription. Upon a determination that vision correction is needed, various types of lenses may be prescribed. The lenses may be spectacles or ophthalmic devices. Another ophthalmic lens device is a contact lens, which may include, but is not limited to rigid gas permeable lenses, soft gas permeable lenses, and silicon hydrogel contact lenses. Lenses may correct most vision defects, including but not limited to hypermetropia, myopia, astigmatism, and/or presbyopia. Additionally, piano lenses may be available for individuals irrespective of whether corrective lenses are needed. Piano lenses may be used to change or enhance the appearance of the eye, such as for example, changing the color of the iris.

Although a practitioner may be able to order a patient's lenses directly, in some cases, patients may be required to take his/her prescription to a separate location to be filled. Additionally, some patients may wish to order their lenses from other sources, such as discount lens sources. The present invention, in some embodiments, may be used to fill or transmit a contact lens prescription.

In countries where contact lenses are not considered to be medical devices or do not require a prescription, the present invention provides a quick and convenient method to obtain contact lens information, including sphere and cylinder corrections as well as a means to order lenses. In countries in which a prescription is required, the present invention may provide more basic information, such as whether vision correction is needed.

In an alternative embodiment of the present invention, the method and apparatus may be comprised of smaller subsystems with discrete functions. In a preferred embodiment, the general hardware components or subsystems may be a mechanized screening device, a microprocessor, a shell, a WAN/LAN connection (including but not limited to a wireless connection), a visual communication means, an audio communication means, and/or a printer. The visual communication means may include a video screen, a keyboard, and/or a touch screen. The mechanized screening devices will be described in further detail. Other embodiments may also include cameras, particularly digital cameras. In a preferred embodiment, the general software components or subsystems may include system software, credit and coin payment mechanisms, remote management software, and a customer relationship management (CRM) system.

Figure 1A:
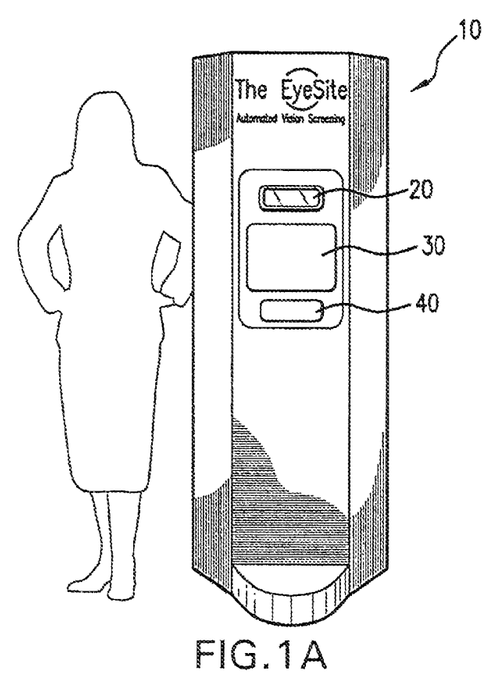
FIG. 1A illustrates an overview of one embodiment of a kiosk device in accordance with the present invention.

For example, a vision screening kiosk 10 may have an external construction as shown in FIG. 1A. In one embodiment, the kiosk may be portable. The vision screening kiosk may have an eye cup 20 that is designed to surround the ocular region of the face. The eye cup may be located at any height, or may have an adjustable height to accommodate all heights, including a seated position. Kiosk 10 may also have a touch screen 30 or similar dynamic visual communication means. Eye cup 20 may also comprise disposable components such as paper sleeves or plastic covers for hygienic purposes.

Figure 1B:
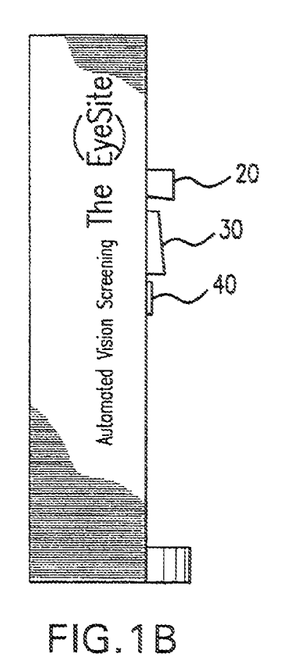
FIG. 1B shows a side view of the kiosk device of the FIG. 1A embodiment.
Figure 1C:
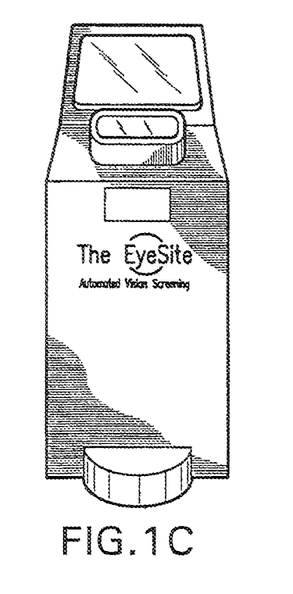
FIG. 1C illustrates an overview of another embodiment of a kiosk device in accordance with the present invention.
Figure 1D:
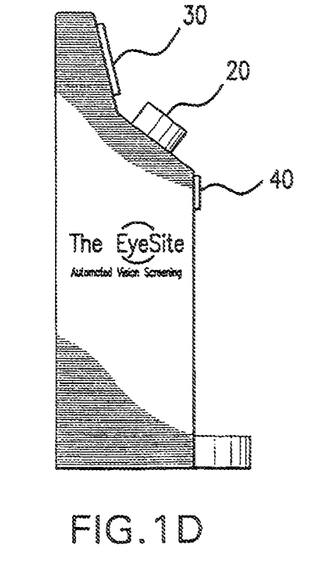
FIG. 1D shows a side view of the kiosk device of the FIG. 1C embodiment.

As shown in FIGS. 1B and 1D, kiosk 10 may also have a printer and payment area 40. This area preferably provides the user with transaction-authorizing equipment such as a credit card interface that is adapted to read the identification data, from the customer credit card and then dial into the card-issuing entity to request payment authorization for the transaction as is commonly known by those of skill in the art. The user can pass the identification card through a magnetic card reader that reads the stored transaction information and a controller can cause the stored transaction(s) to be displayed so that a purchaser can select a transaction for execution. The purchaser may enter a single input to select a transaction, thereby simplifying and further expediting the transaction and automated processing thereof. The transaction parameters may include one or more of the form of payment (debit card, credit card, coin, currency, health incurance, Smart-Card® etc.) and whether or not a receipt should be printed upon completion of the transaction. An example of such a system is produced by NetShift (Newbury, U.K.). This area also optionally includes a printer that when activated, dispenses personal vision screening results. In another embodiment other forms of result, such as a plastic "Smart Card" may be dispensed. In a related embodiment, a purchaser may use an insurance card to receive a discounted or free exam.

The vision kiosk is preferably connected, to the internet by any means known in the art, including a wireless connection and is adapted to receive updates such as manufacturer promotions or additional participating eye care practitioners. The kiosk may also, if requested by the user, transmit screening results to an eye care practitioner or a web address. In another embodiment, the user may transmit screening results to a contact lens supplier and order appropriate products. Additionally, the user may use the screening results to select a set of spectacles, such as bifocals, for example. In this embodiment, the test results may include sphere and cylinder correction, or may indicate the appropriate display rack from which the user may select the appropriate vision correction. In this embodiment, the display rack has preferably been categorized for such use.

The kiosk may be of any shape or size. As commonly understood, the kiosk is a self-contained small area set off by walls. It may be free standing or incorporated into a structure. Various kiosk designs are shown in FIGS. 3A-3C and 4A-4D. For example, in one embodiment, the kiosk may be an open or enclosed booth that a user may walk into. In another embodiment, the kiosk may include one or more seats. In another embodiment, the kiosk may be small enough to sit on a counter-top. The kiosk screen may be oriented for a seated or upright user, and/or may be adjustable for both positions. The kiosk may also include partitions for a user's belongings, such as shopping bags, keys, or a handbag. The kiosk may also have disposable protective sleeves or coverings over certain parts for hygiene purposes. The kiosk may also be adapted to store and sort a limited number of lenses, such as piano lenses, for example.

The present invention may perform subjective and/or objective vision tests to determine visual acuity, contrast sensitivity, eye topography, eye health, and/or similar parameters. Subjective tests may include tests for contrast sensitivity and visual acuity. Objective tests may include test to determine optical power, the curvature of the eye, and the surface topography of the eye. Additionally, a red/green test may be used to determine color vision deficiency. The present invention may also provide other useful functions related to cosmetic appearance and eye health. Some of these functions may include a virtual model that allows a user to view him/herself with particular vision correction options, such as color contact lenses. The virtual model can be created through the use of a camera mounted into the kiosk and connected to facial recreation software. Alternatively, virtual software can be included which creates a digital representation of a user with a particular type of colored lens. In a related embodiment, the kiosk may be adapted to dispense piano or color contact lenses to a user as a part of, or separate from, an eye care or full face makeover. The example embodiment is designed to be operated by a user (subject) without assistance from another person, including an ophthalmologist. A user is capable of completing the vision acuity exam completely by himself/herself.

Figure 6:
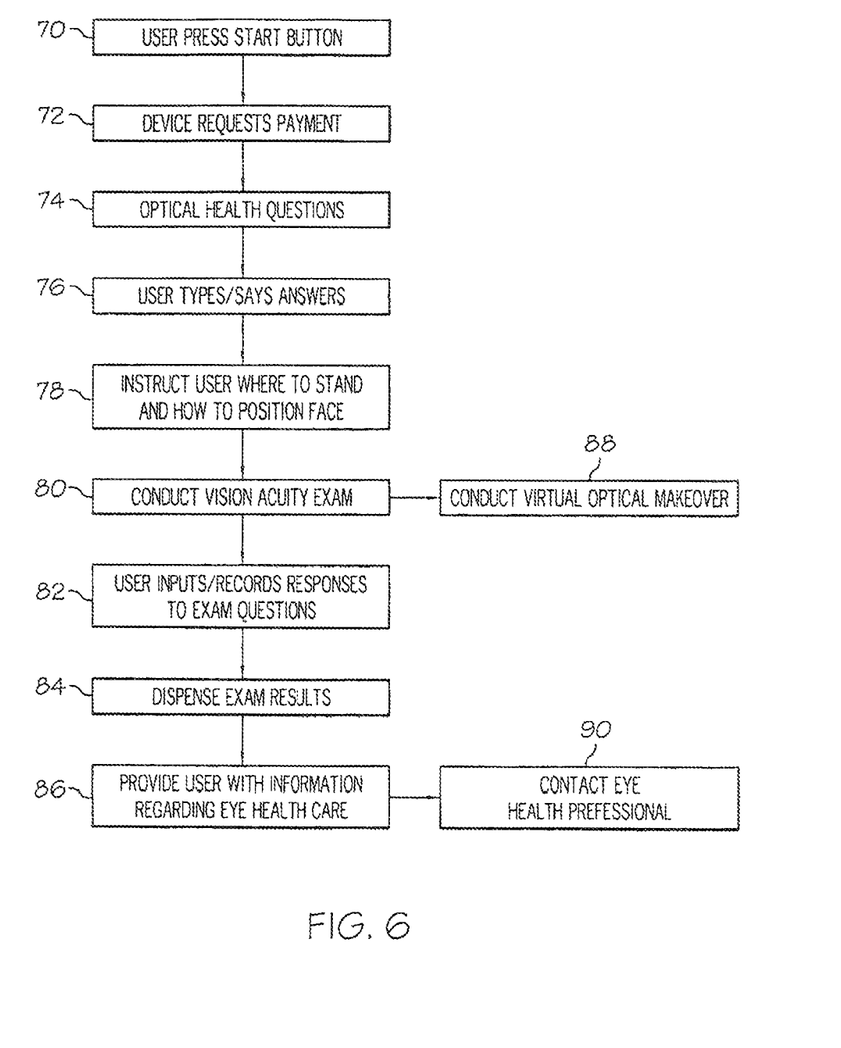
FIG. 6 shows a flow chart of the steps involved in the vision acuity exam.

As shown in FIG. 6 the test process incorporates multiple steps, which may be completed in any logical order. The tests may be operated in any chosen language. The following order is exemplary only. To begin the test process, a user may touch 70 a start button displayed on a touch screen or other input/output device. In one embodiment, payment may be requested 72 immediately after the user indicates that he is ready to start. In another embodiment, a series of questions 74 may precede the request for payment. Alternatively, no payment is required. These questions 74 are preferably designed to elicit the known optical health of the consumer. Questions 74 can be displayed on a display screen or other output device, or can be audio played over speakers. Answers 76 can be typed on a keypad or entered on touchscreen input device or spoken with voice recognition. Exemplary questions 74 may include "How long has it been since your last eye exam?"; "Do you wear corrective lenses?" "Are you wearing corrective lenses at this time?"; "What is your age?"; "Do you or any members of your family have glaucoma?"; "Do you play sports?"; "Do you have macular degeneration"; "For what purpose a user wears glasses?"; "What type of lenses a user wears?"; "Approximate date of the user's last visit to an ophthalmologist?"; "The user's family eye health history?"; "Whether the user suffers from other health issues such as hay fever, allergies, dry eye syndrome or watery eye syndrome?"; "Whether a user has had corrective eye surgery such as laser surgery?"; etc. More than one question may be displayed on the screen at one time. In an embodiment that asks questions before payment, specific answers to questions may cause a disclaimer to be shown to the user that may indicate whether the auto eye exam is appropriate for the user.

The example embodiment can instruct 78 the user as to where to stand and how to position their face relative to the eye cup. In an embodiment that does not include an eye cup, the user can be instructed 78 to focus on an image projected on a screen. In an embodiment without an eye cup, the invention preferably instructs the user where to sit or stand, such as for example, by providing foot print shadows or adhesive on the floor to indicate where the user should place his or her feet.

The example embodiment can test 80 various vision components with varying levels of technology. In one embodiment, Snellen or other vision targets may be projected onto the screen in a format that is equivalent to reading the chart at a distance of 20 feet. The user can then be asked to type in the last row of letters that are visible to him or her. In an alternative embodiment, the software can ask the user if he/she can read the third line from the top, etc. The user then inputs 82 his or her answer, via a touch screen keyboard or traditional keyboard. In another embodiment, the user can respond verbally to verbal and/or visual questions. The software may then records 82 the results of this visual acuity test. In another embodiment, the kiosk may test 80 contrast sensitivity by projecting images on the screen. The images can comprise vertical black and white stripes of varying thickness. If the stripes are very thin, individual stripes will not be visible. Only a gray image is visible. As the stripes then become wider, there is a threshold width from where it is possible to distinguish the stripes. The user is asked if he can see any lines and if so, which direction are they pointing to. These results may also be recorded 82 and may be dispensed 84 to the user.

In a more sophisticated device, the aforementioned subjective tests 80 may be used with objective tests, including tests performed by an automated adaptive optic phoropter, a badal optometer, a topographer, a tonomer, a wavefront sensor, and/or fundus camera (retinal photograph). Any combination of these tests may be used to measure various attributes of the eye including sphere, cylinder, and cylinder axis, and the curvature of the eye. The tests 80 may be used alone for completely objective tests or they may be combined with the subjective tests already described. In still another embodiment, the tests that are described in U.S. Pat. No. 5,914,772 may be used. In an advanced embodiment, an adaptive optics phorometer may be used. In this embodiment, a user may be asked to look into a full color screen. An automated phoropter, in combination with other instruments, such as a wavefront sensor, may examine the eye to determine the refractive errors on the eye. The adaptive optics technology may then use the measured topography of the user's eye to generate a screen that, when viewed by the user, displays the image in a corrected form for that particular user. The user may then be asked to evaluate the clarity of the image and approve whether it is satisfactory.

An example embodiment can provide a user with information 86 regarding corrective lens options, referrals to opticians, and may also provide an on-line means to locate and make an appointment with an eye care professional. The example embodiment may also provide a map to the closest eye care professional. The output can be on screen, printed, audio and downloaded to a PDA device. The example embodiment may also be able to transmit the results of the self-screen via internet, phone lines and/or wireless communication to the practitioner in advance of the appointment. If the user already has an ophthalmologist the user can enter his/her name and contact information. Alternatively, the user is prompted a list of ophthalmologists from which the user may choose. Alternatively, the user can enter his/her zip code or address to produce a list of ophthalmologists nearest to the user. The user can choose a particular ophthalmologist by touching a name on the screen. A next screen loads and requests further contact information from the user. The user then enters his/her contact information such as telephone number, address and email address. When the user has entered the contact information, a confirmation screen is loaded. The user can receive a copy of the confirmation via email or have it printed. The chosen, ophthalmologist can be contacted 90 with the user's information. Additionally, in some countries, the example embodiment may provide a direct link to a third party distributor to enable the user to purchase lenses directly or may dispense lenses.

Additionally, the example embodiment may be used in connection with a website and/or national database. Each remote kiosk has applications and can have a local database. A central server contains applications, and a database that can be accessed by remote kiosk via connections, respectively, over a network. The server runs administrative software for a computer network and controls access to itself and database. The remote kiosk may access the database over a network, such as but not limited to: the Internet, a local area network (LAN), a wide area network (WAN), via a telephone line using a modem (POTS), Bluetooth, WiFi, cellular, optical, satellite, RF, Ethernet, magnetic induction, coax, RS-485, the like or other like networks. The server may also be connected to the local area network (LAN) within an organization. In this embodiment, data obtained at the kiosk may be inputted into a patient database that may be accessible by a user and/or the user's eye care professional. The user may check his or her optical history online. Additionally, an eye care professional may update the database with information, such as the user's current prescription. The website may also answer questions, direct users to eye care professionals, provide locations of screening kiosks, and provide eyecare and eye wear options. The example embodiment can further comprise executable software code and computer readable media having code resident thereon for carrying out the steps of a vision acuity exam.

In still another embodiment, the user can be shown information 86 about a variety of eye health conditions such as cataracts, diabetes, floaters, glaucoma, macular degeneration, presbyopia, dry eye syndrome, watery eye syndrome, and refractive error. The user may select to learn more about one of these conditions by touching the particular condition on the screen. A next screen will load that provides significant information about the condition. The user may print the information.

In still another embodiment, the kiosk may also provide a virtual optical makeover 88. In this embodiment, the user's photograph may be obtained via an outboard camera, uploaded, or through other means and projected onto a screen. The user may then select different eyewear, including colored lenses or spectacles. In this embodiment, the image of the user taken by the camera may be altered according to the user's selection. For example, a user with brown eyes may select corrective lenses with color. The projected image of the user may then be altered to show the user with blue eyes, green eyes, etc. The user may also select various types of spectacles. In this case, the projected image of the use may then be altered to show the user wearing a particular spectacle style. In an alternative embodiment, the kiosk may provide a full facial makeover, including eyewear, makeup and the like. In a related embodiment, the kiosk may be adapted to dispense piano or color contact lenses to a user as a part of, or separate from, the eye care or full face makeover.

Many types of contact lenses may be available for a particular user and their use is recommended dependent upon the optical topography of the user's eye. For example, a user may be a presbyope with astigmatism. In some embodiments, the present invention may make recommendations as to the type of vision correction needed as well as any vision correcting options that are applicable to the particular user, in terms of different brands, different product lines, different types of corrective lenses and surgical or nonsurgical visual correction options.

Figure 2:
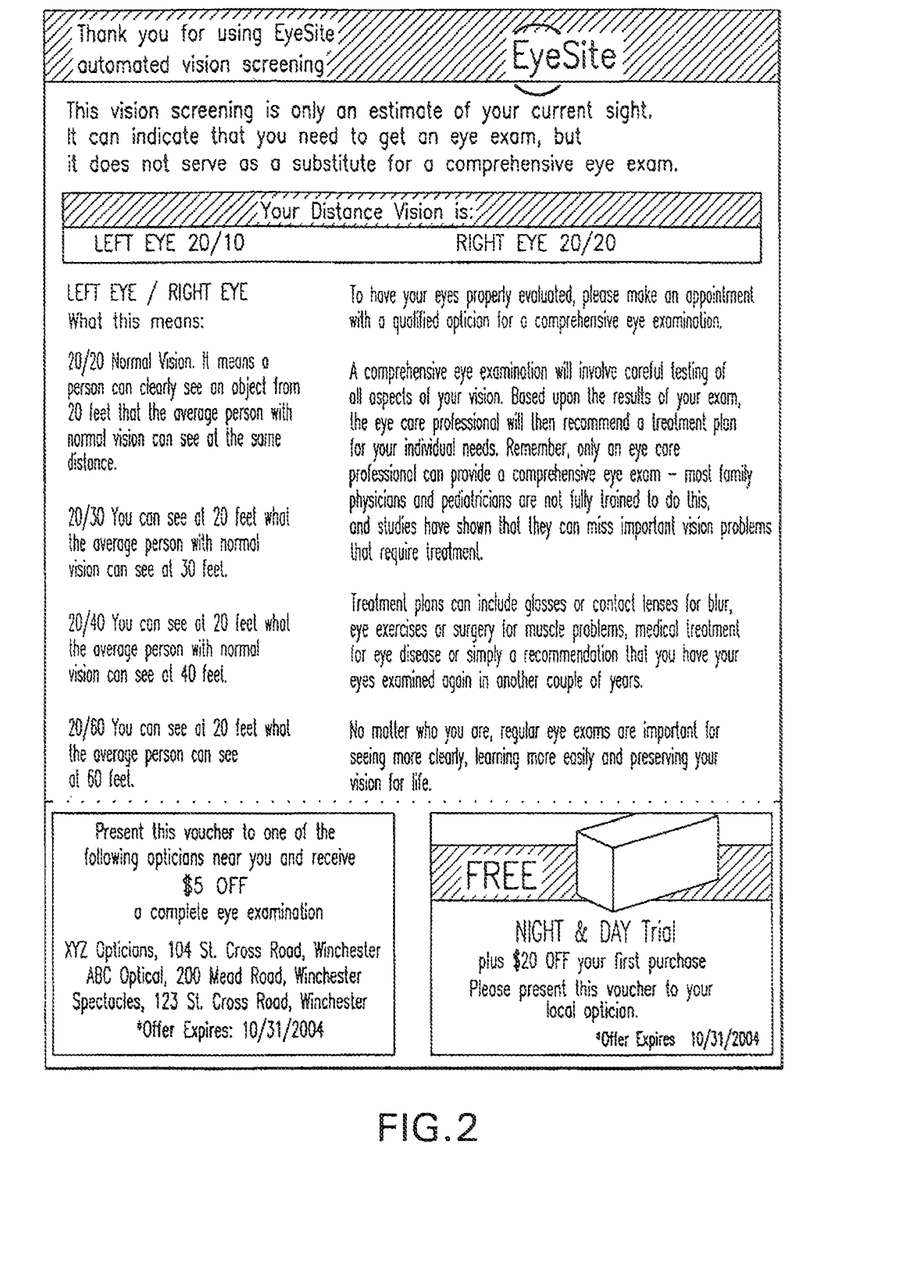
FIG. 2 depicts one embodiment of a printed report generated by the present invention.
Figure 3A:
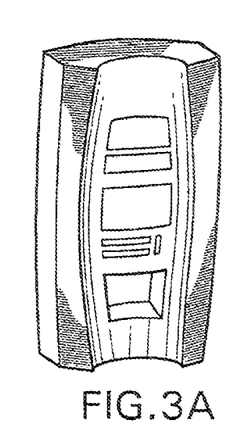
FIG. 3A depicts a kiosk design according to the present invention.
Figure 3B:
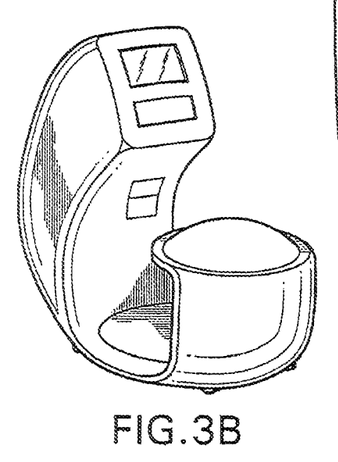
FIG. 3B depicts another kiosk design according to the present invention.
Figure 3C:
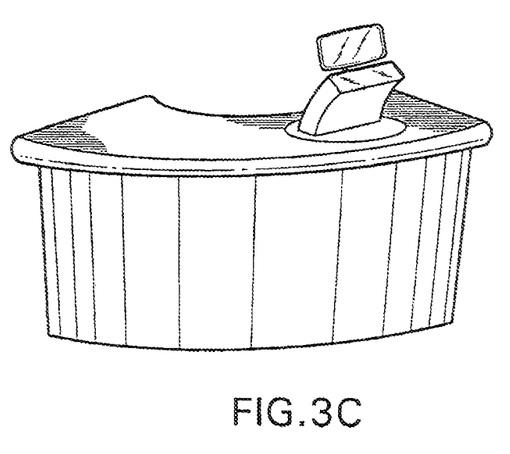
FIG. 3C depicts another kiosk design according to the present invention.
Figure 4A:
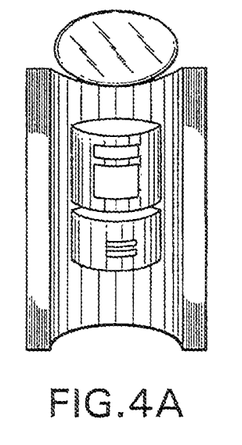
FIG. 4A depicts another kiosk design according to the present invention.
Figure 4B:
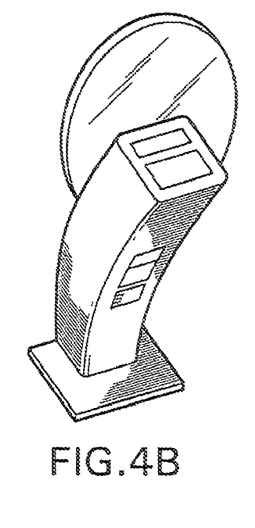
FIG. 4B depicts another kiosk design according to the present invention.
Figure 4C:
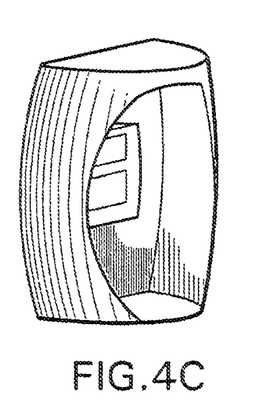
FIG. 4C depicts another kiosk design according to the present invention.
Figure 4D:
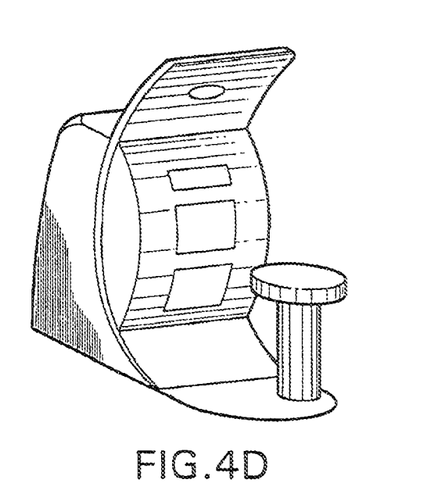
FIG. 4D depicts another kiosk design according to the present invention.

In one embodiment of the present invention, test results may be printed for the user. An example of such a printout is shown in FIG. 2. In this embodiment, the report preferably includes one or more of the following: whether vision correction is needed, the level of vision correction needed for both the left and right eye, basic eye health information, legal driving requirements from the Department of Motor Vehicles (DMV), frequently asked questions, nearby participating eye care practitioners, recommended products, recommended manufacturers, and manufacturer discounts. The report preferably contains a disclaimer that states, for example, "This is not a complete eye exam" and instructs the user to see an eye care professional for a more complete exam. The printout may also contain explanations of different types of corrective options and/or cosmetic options.

In one embodiment, a plastic card, such as for example, a SmartCard® with a computer chip, bar code, magnetic strip, or any other means of storing data may be issued to the user. The SmartCard® may have confidential information embedded on it such as prescription information, prescription history, user identification, retinal photographs, preferred type of lenses, and promotional offers. Such information may be encrypted or imbedded in the card, similar to a Common Access Card (CAC) used in military applications. In an extended embodiment, this card may be updated remotely by an eye care practitioner. In still another embodiment, this card may be scanned at a kiosk for further transactions, such as refilling/ordering lenses for a current prescription, scheduling eye care appointments, and/or accessing user eye history.

In an example embodiment, the vision acuity tests can be performed through the use of a plurality of mirrors mounted at particular angles on a box to define an optical path. An example embodiment of a mirror box 50 is shown in FIGS. 5A-5D. The example embodiment has a front 52, a back 54, a right and left side, a bottom and a top. A viewing window 56 is located on the upper section of the front surface. This window 56 can be made of glass or plastic or other optically transparent material. Additionally, a view finder 58 extends outwardly from the window 56. A user can look through the window 56 by looking into the end of the view finder 58. Alternatively, a user can look directly at the window 56. It is contemplated that either with a view finder 56 or without, a user is about 20 inches from the window 56 for proper use. Thus, an example length of the view finder 58 extending from the window 56 is about 20 inches. The example embodiment has a height (top to bottom) of about thirty inches and a depth (front to back) of about 20 inches. The mirror box 50 can be secured within a kiosk through mounting rails 72 on both sides of the box 50.

The box can be inserted into the kiosk such that it is removable from the kiosk entirely. The mirror box simulates looking down a long hallway or a significant distance from a stimulus to the subject. The mirror box works in such a way that an internal stimulus projects characters in varying sizes. An example of the stimulus is an LCD screen. An example of characters are Sloan letters often used in Snellen tests. An image is projected from the stimulus across a plurality of mirrors. An example of the range of amount of mirrors is between 4 mirrors and 9 mirrors. The example embodiment is shown with 4 mirrors.

Figure 5A:
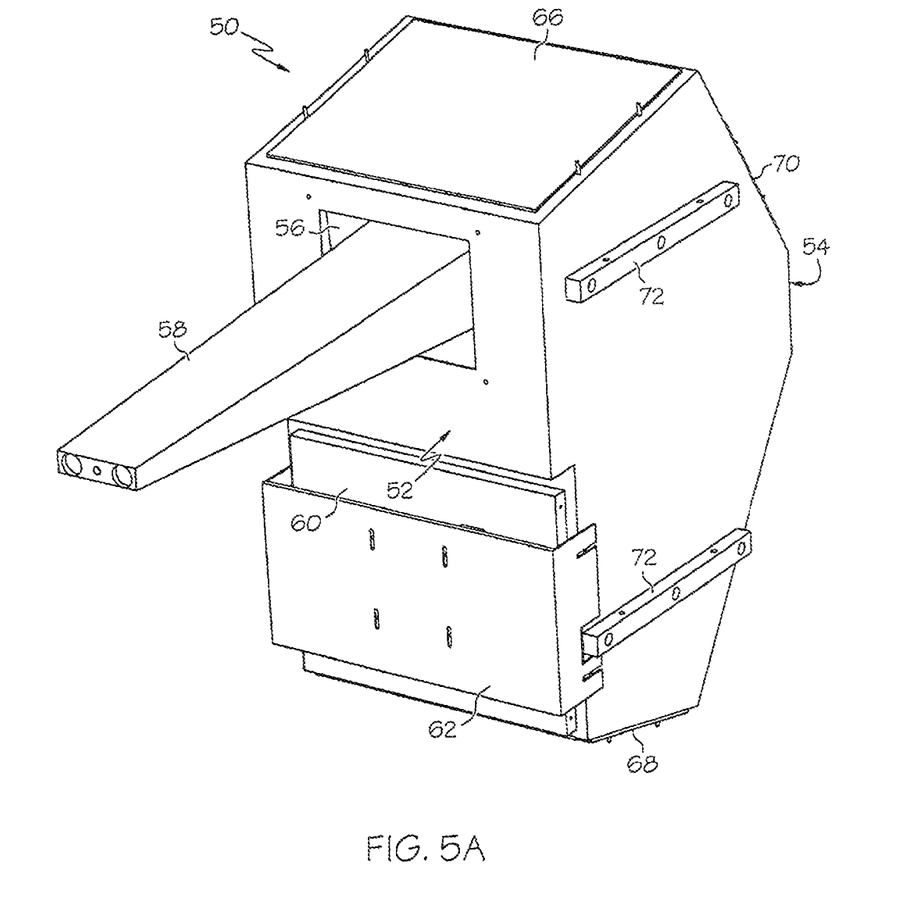
FIG. 5A shows a front perspective view of a mirror box component of the kiosk device in accordance with the present invention.
Figure 5B:
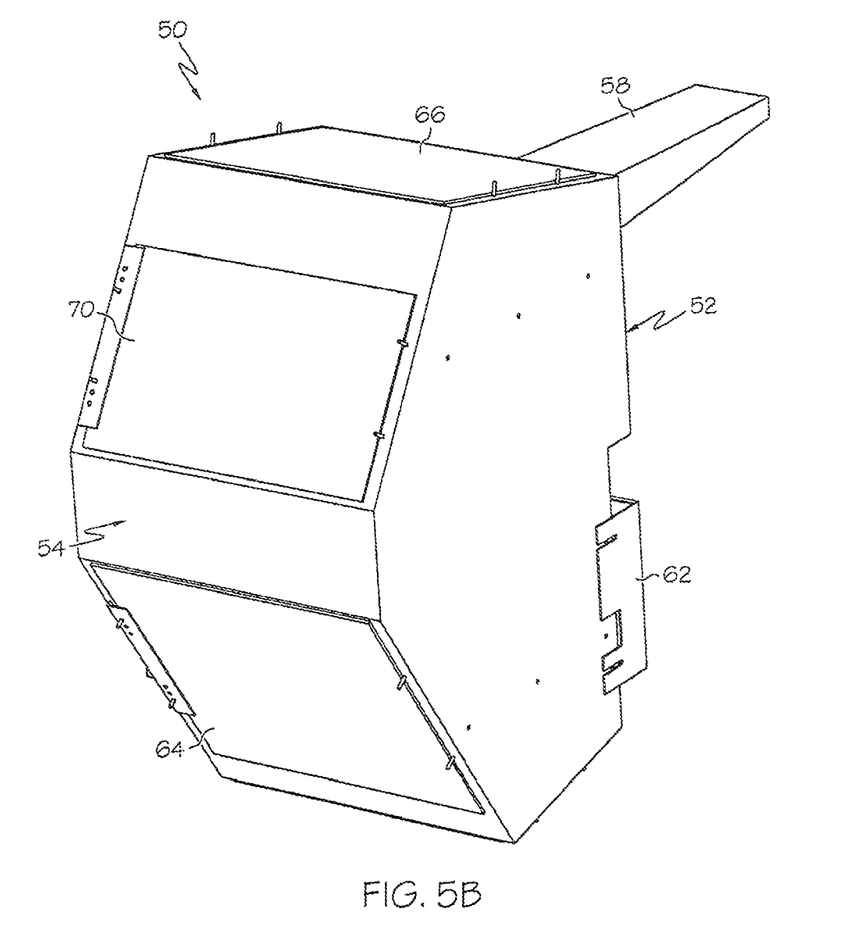
FIG. 5B shows a rear perspective view of the mirror box component shown in FIG. 5A.
Figure 5C:
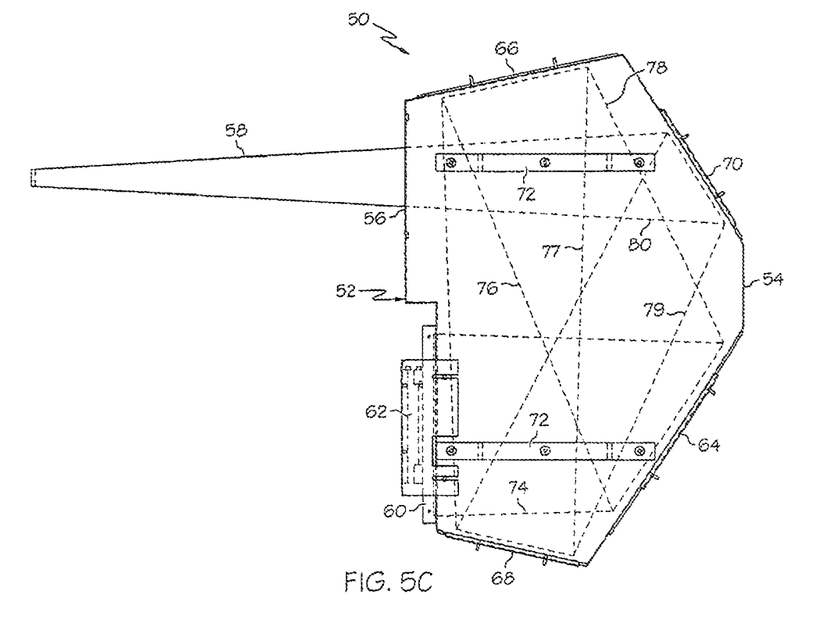
FIG. 5C shows a cross sectional view of the mirror box component shown in FIG. 5A, with optical paths in broken lines.
Figure 5D:
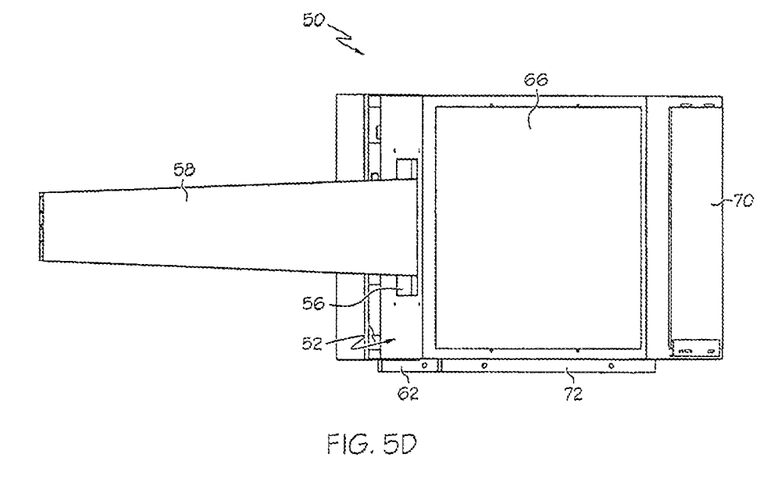
FIG. 5D shows a top plan view of the mirror box component shown in FIG. 5A.

The window 56 is located directly above a stimulus 60, such as a display screen, projector, or other image generating means. The stimulus 60 is secured to the interior of the front side 52 and faces toward the rear side. The stimulus 60 can be secured with a mounting device 62 such as a mounting bracket or face shield. The stimulus 60 faces the opposite direction from the position of a user. As shown in FIG. 5C, the stimulus 60 projects an image along path 74 toward a first mirror 64 mounted at a first angle of between −140° and −150° to vertical. In the example embodiment the first mirror 64 is positioned at −147° to vertical. The image is then reflected from the first mirror 64 along path 76 onto a second mirror 66 positioned at a second angle between 70° and 80° to vertical. In the example embodiment the second mirror 66 is positioned at 78° to vertical. The image is then reflected from the second mirror 66 along path 77 onto a third mirror 68 positioned at a third angle of between 100° and 110° from vertical. In the example embodiment the third mirror 68 is positioned at 103° to vertical. The image is then reflected from the third mirror 68 along path 79 onto a fourth mirror 70 positioned at a fourth angle of between 105° and 115° to vertical. In the example embodiment the fourth mirror 70 is positioned at 110° to vertical. The image is then reflected from the fourth mirror 70 along path 80 toward the window 56 and in the direction of a user.

In the example embodiment the total distance ("optical path") traveled by the image between the stimulus 60 and the position of the user is greater than ten. Providing a distance of ten feet or greater reduces the amount of induced myopia to the user. Further, the user can take an accurate distance vision test that would otherwise require a large room. All of the mirrors can be contained in a single mirror box.

The invention has been described in detail, with particular reference to certain preferred embodiments, in order to enable the reader to practice the invention without undue experimentation. A person having ordinary skill in the art will readily recognize that many of the previous components, compositions, and/or parameters may be varied or modified to a reasonable extent without departing from the scope and spirit of the invention. Furthermore, titles, headings, example materials or the like are provided to enhance the reader's comprehension of this document, and should not be read as limiting the scope of the present invention. Accordingly, the invention is defined by the following claims, and reasonable extensions and equivalents thereof.

What is claimed is:

1. A method for screening vision using a kiosk comprising:
   requesting, using the kiosk, user information;
   performing objective visual acuity tests using the kiosk, wherein said visual acuity tests determine: sphere, cylinder, cylinder axis, or corneal curvature, or any combination thereof; and
   reporting visual acuity results:
   wherein said method does not require assistance from another person.

2. The method of claim 1, further comprising performing one or more eye health tests using the kiosk or using information obtained from the kiosk.

3. The method of claim 1, further comprising performing one or more contact sensitivity tests using the kiosk or using information obtained from the kiosk.

4. The method of claim 1, further comprising dispensing one or more lenses using the kiosk or using information obtained from the kiosk.

5. The method of claim 1, further comprising receiving the user information using the kiosk.

6. The method of claim 5, wherein the user information is received via a touch screen.

7. The method of claim 1, further comprising sending, with the kiosk, the user information, the visual acuity results, or any combination thereof to a remote location.

8. The method of claim 7, wherein the user information, the visual acuity results, or the combination thereof is sent to the remote location via an internet connection, a telephone connection, a wireless connection, or any combination thereof.

9. The method of claim 7, wherein the remote location is an eye care practitioner, an eyewear supplier, a web address, or any combination thereof.

10. The method of claim 1, further comprising dispensing, with the kiosk, disposable components for hygienic purposes.

11. The method of claim 1, further comprising receiving, with the kiosk, a payment.

12. The method of claim 1, further comprising performing, with the kiosk, a virtual makeover based on the user information, the visual acuity results, or any combination thereof.

13. The method of claim 1, further comprising:
    creating, with the kiosk, a smart card containing the user information, the visual acuity results, or any combination thereof; and
    dispensing, with the kiosk, the smart card.

14. The method of claim 1, wherein reporting the visual acuity results comprises printing the visual acuity results.

* * * * *